United States Patent [19]

Kujawski et al.

[11] Patent Number: 4,568,330

[45] Date of Patent: Feb. 4, 1986

[54] CARDIOPLEGIA DELIVERY SYSTEM WITH IMPROVED BUBBLE TRAP

[75] Inventors: Dennis M. Kujawski, Ypsilanti; Patti L. Parrott, Dexter, both of Mich.

[73] Assignee: Minnesota Mining and Manufacturing Company, Saint Paul, Minn.

[21] Appl. No.: 500,525

[22] Filed: Jun. 2, 1983

[51] Int. Cl.[4] .......................... A61M 1/03; B01D 19/02
[52] U.S. Cl. .......................................... 604/53; 604/4; 604/113; 604/122; 604/406; 128/DIG. 3
[58] Field of Search .......................................... 604/4–7, 604/113, 118, 122, 406; 128/399, 400, 674, 684, DIG. 3

[56] References Cited

U.S. PATENT DOCUMENTS

| | | | |
|---|---|---|---|
| 3,062,202 | 11/1962 | Hyman et al. | 128/674 |
| 3,374,066 | 3/1968 | Farrant | 604/122 |
| 3,504,674 | 4/1970 | Swenson et al. | |
| 3,513,845 | 5/1970 | Chesnut et al. | 604/4 |
| 3,907,504 | 9/1975 | Hammond et al. | |
| 3,927,980 | 12/1975 | Leonard | |
| 3,963,024 | 6/1976 | Goldowsky | |
| 4,062,360 | 12/1977 | Bentley | |
| 4,227,525 | 10/1980 | Lundquist | |
| 4,249,923 | 2/1981 | Walda | |
| 4,333,454 | 6/1982 | Hargest, III | |
| 4,338,933 | 7/1982 | Bayard et al. | |
| 4,427,009 | 1/1984 | Wells et al. | 604/113 |
| 4,433,971 | 2/1984 | Lindsay et al. | 604/118 |

Primary Examiner—C. Fred Rosenbaum
Assistant Examiner—Michelle N. Lester
Attorney, Agent, or Firm—Donald M. Sell; James A. Smith; Jennie G. Boeder

[57] ABSTRACT

A cardioplegia system in which cardioplegia medication or a mixture of arterial blood and medication is delivered to the heart of a patient undergoing open heart surgery, which includes a bubble trap in conjunction with the delivery system. The bubble trap separates bubbles from the cardioplegic solution and when formed at least partially of transparent material, provides a visual indication of the air removed from the infusion liquid.

19 Claims, 7 Drawing Figures

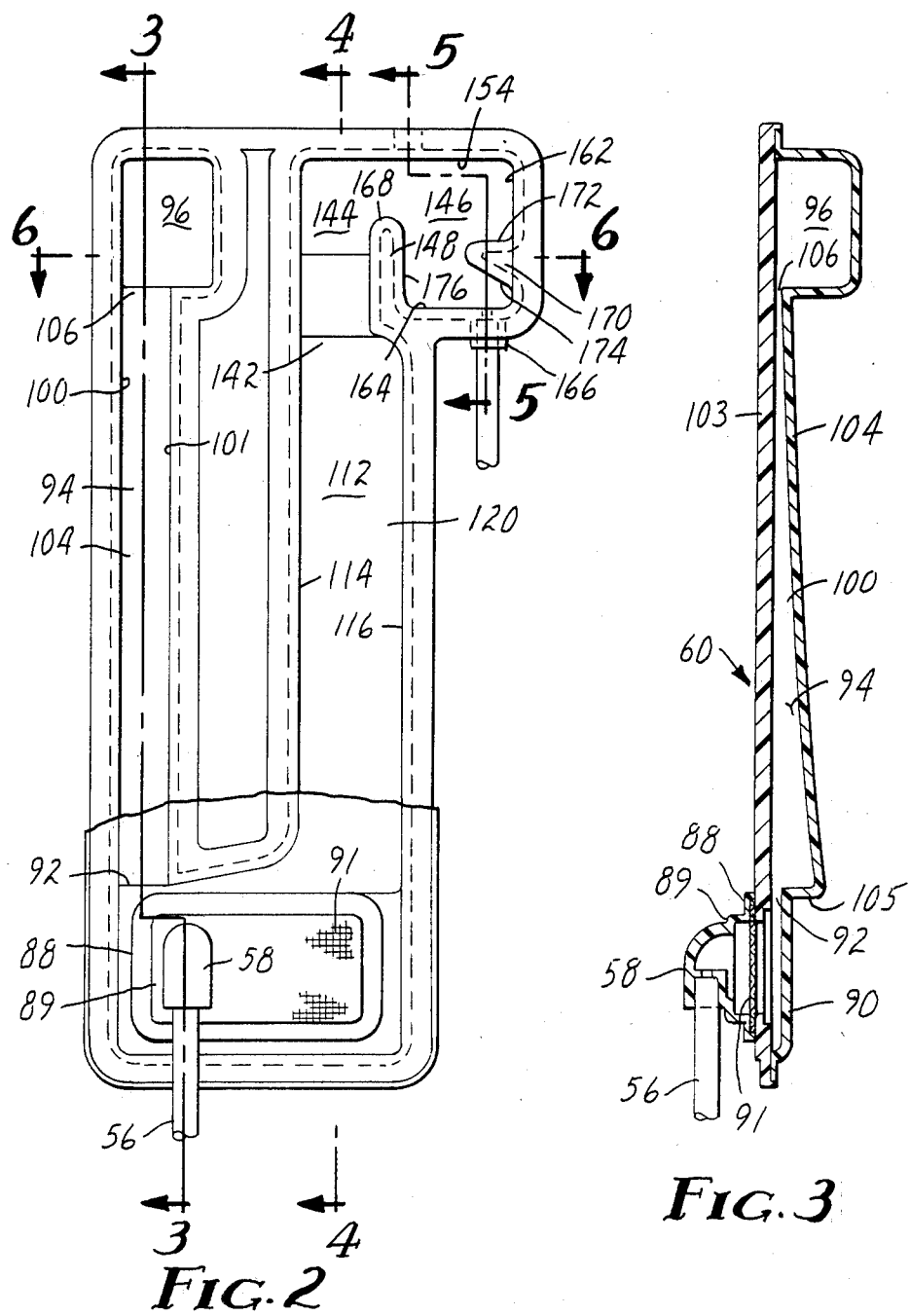

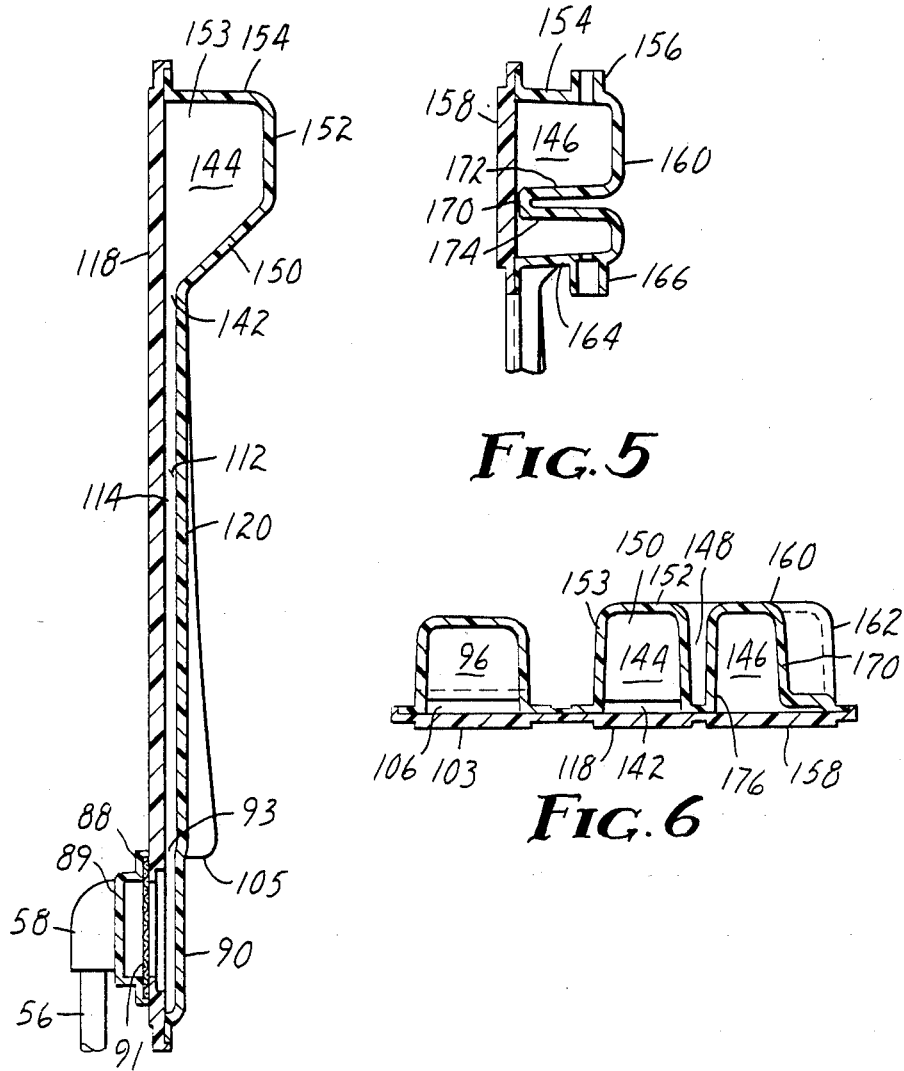

CARDIOPLEGIA DELIVERY SYSTEM WITH IMPROVED BUBBLE TRAP

FIELD OF THE INVENTION

This invention relates to extracorporeal support systems for cardiovascular surgery, and particularly to methods and apparatus for cooling and administering drugs to the heart during open heart surgery to provide myocardial protection. More particularly, the invention relates to a cardioplegia system which includes a bubble trap in conjunction with the delivery system. The bubble trap separates air from the arterial flow and when formed from transparent material, provides a visual indication of the increase of air in the system. Preferably, the bubble trap is included in a one-piece monitoring module which further includes a filtering assembly, a temperature monitor and a pressure monitor.

BACKGROUND OF THE INVENTION

Open heart surgery has been practiced for a number of years and techniques for protection of the patient have been under study for all of this period. When the blood of the patient is by-passed to an extracorporeal support system which maintains the pumping function of the heart and the oxygenation function of the lungs, it is important that the heart itself be protected from damage. In the circumstances of heart surgery, the possibility of damage to the heart is greatly reduced by cooling and administering drugs to the heart in a technique called "clear" or "crystalloid" cardioplegia. Another method of cardioplegia is "blood" cardioplegia wherein the actual blood of the patient is used to cool the heart and as the vehicle for delivery of the cardioplegic solution.

Various methods for achieving cardioplegia have been used. Literature on the subject includes:

*A Simple Method of Cold Coronary Perfusion*, Hillel Lakes, M.D. et al. The Annals of Thoracic Surgery, Vol. 25, No. 4, April 1978

*Cold Cardioplegia Versus Hypothermia for Myocardial Protection*, The Journal of Thoracic and Cardiovascular Surgery, Vol. 76, No. 5, November 1978

Additionally, cardioplegia delivery systems have been disclosed in commonly assigned U.S. patents, U.S. Pat. No. 4,433,971; U.S. Pat. No. 4,427,009; and U.S. Pat. No. 4,416,280. In all of these systems the cardioplegia fluid is pumped through a tube set, cooled, debubbled, and the pressure and temperature of the fluid are measured before it is delivered to the patient through a cannula.

SUMMARY OF THE INVENTION

The present invention relates to an improved system for achieving cardioplegia which is utilized along with an extracorporeal life support system in a combined plan making it easier to safely administer the cold oxygenated blood and/or cardioplegia medication.

The present invention provides a bubble trap for removing bubbles from a liquid comprising:

(a) a primary chamber having an entrance way for liquid disposed at the bottom, said primary chamber capable of providing a passageway for liquid leaving said entrance way, and said primary chamber having a greater cross-sectional area than said entrance way, such that when liquid enters said primary chamber from said entrance way the average velocity of the liquid is caused to decelerate; and (b) a secondary chamber separated from said primary chamber by a dam, the area above said dam providing a passageway for liquid flowing from said primary chamber to said secondary chamber, said secondary chamber having a shelf extending into said secondary chamber in a direction towards said dam, but not extending so far into said secondary chamber as to block the passage of liquids through said secondary chamber, and said secondary chamber having an outlet for liquid disposed at the bottom of said secondary chamber.

The present invention also provides an improved cardioplegia system in which cardioplegia medication or a mixture of arterial blood and medication is delivered to the heart of a patient during open heart surgery, wherein the improvement comprises a bubble trap for removing bubbles from the infusion fluid, said bubble trap having an infusion fluid inlet connected to the supply of cardioplegic infusion fluid and an outlet leading to the heart cannula, and said bubble trap comprising:

(a) a primary chamber having an entrance way for infusion fluid disposed at the bottom, said entrance way adapted for connection with said infusion fluid inlet, said primary chamber capable of providing a passageway for infusion fluid leaving said entrance way, and said primary chamber having a greater cross-sectional area than said entrance way, such that when infusion fluid enters said primary chamber from said entrance way the average velocity of said infusion fluid is caused to decelerate; and (b) a secondary chamber separated from said primary chamber by a dam, the area above said dam providing a passageway for infusion fluid flowing from said primary chamber to said secondary chamber, said secondary chamber having a shelf extending into said secondary chamber in a direction towards said dam, but not extending so far into said secondary chamber as to block the passage of infusion fluid through said secondary chamber, and said secondary chamber having said outlet for infusion fluid disposed at the bottom of said secondary chamber.

Preferably, the improved bubble trap is associated with a temperature monitor, and serves also in connection with a pressure monitoring system. The bubble trap is preferably transparent to provide a visual indication of the increase of air in the system.

A further improvement lies in an improved pressure monitoring system comprising an at least partially transparent single-leg manometer column which facilitates easy visual indication of the pressure level, and an associated graduated linear manometer scale which enables safer and more readily controlled cardioplegia to be achieved. The manometer column is a compact closed-end column having a sealed reservoir at the top of the column. The pressure monitoring system is preferably constructed of a transparent material to enable easy observation of the infusion fluid level within the manometer column.

A still further feature of the invention lies in the use of a cooling system which utilizes contained cold packs to cool the infusion fluid.

Another improvement lies in the use of an improved temperature monitoring component which is placed adjacent and in thermal contact with the infusion fluid path, and which utilizes a liquid crystal temperature sensing strip which provides a colored visual indication of the temperature of the infusion fluid.

An additional improvement lies in the use of a filtering assembly incorporating a filter which removes particulate matter from the infusion fluid and, thus, prevents the infusion of foreign bodies into the aorta and coronary arteries.

A further improvement lies in the incorporation of the above-described pressure monitoring system, bubble trap, in-line temperature monitoring component, and filtering assembly in a one-piece transparent molded plastic monitoring module. The ability to monitor pressure and temperature without having to hookup additional hardware is a significant time saver.

Other features of the invention will be apparent in the following description and claims, in which the principles of the invention are set forth together with a detailed disclosure of the manner and process of using the invention directed to persons skilled in this art to enable the practice of the invention, all in connection with the best mode presently contemplated for the invention.

BRIEF DESCRIPTION OF THE DRAWINGS

DRAWINGS accompany the disclosure and the various views thereof may be briefly described as:

FIG. 2 is a front elevational view of the one-piece monitoring module of the system, with parts thereof broken away.

FIG. 3 is a side sectional view of the monitoring module on line 3—3 of FIG. 2.

FIG. 4 is a sectional view of the monitoring module on line 4—4 of FIG. 2.

FIG. 5 is a side sectional view of the monitoring module on line 5—5 of FIG. 2.

FIG. 6 is a side sectional view of the monitoring module on line 6—6 of FIG. 2.

DETAILED DESCRIPTION OF THE INVENTION AND THE MANNER AND PROCESS OF USING IT

Reference is made to the following commonly U.S. patents: (1) U.S. Pat. No. 4,433,971 wherein an Integrated Cardioplegia Delivery System including an improved bubble trap is described; U.S. Pat. No. 4,427,009 wherein an Integrated Cardioplegia Delivery System including an improved cooling system is described; and U.S. Pat. No. 4,416,280 wherein a Continuous Cardioplegia Delivery System is described.

The Cardioplegia Delivery System in General

Figure 1:
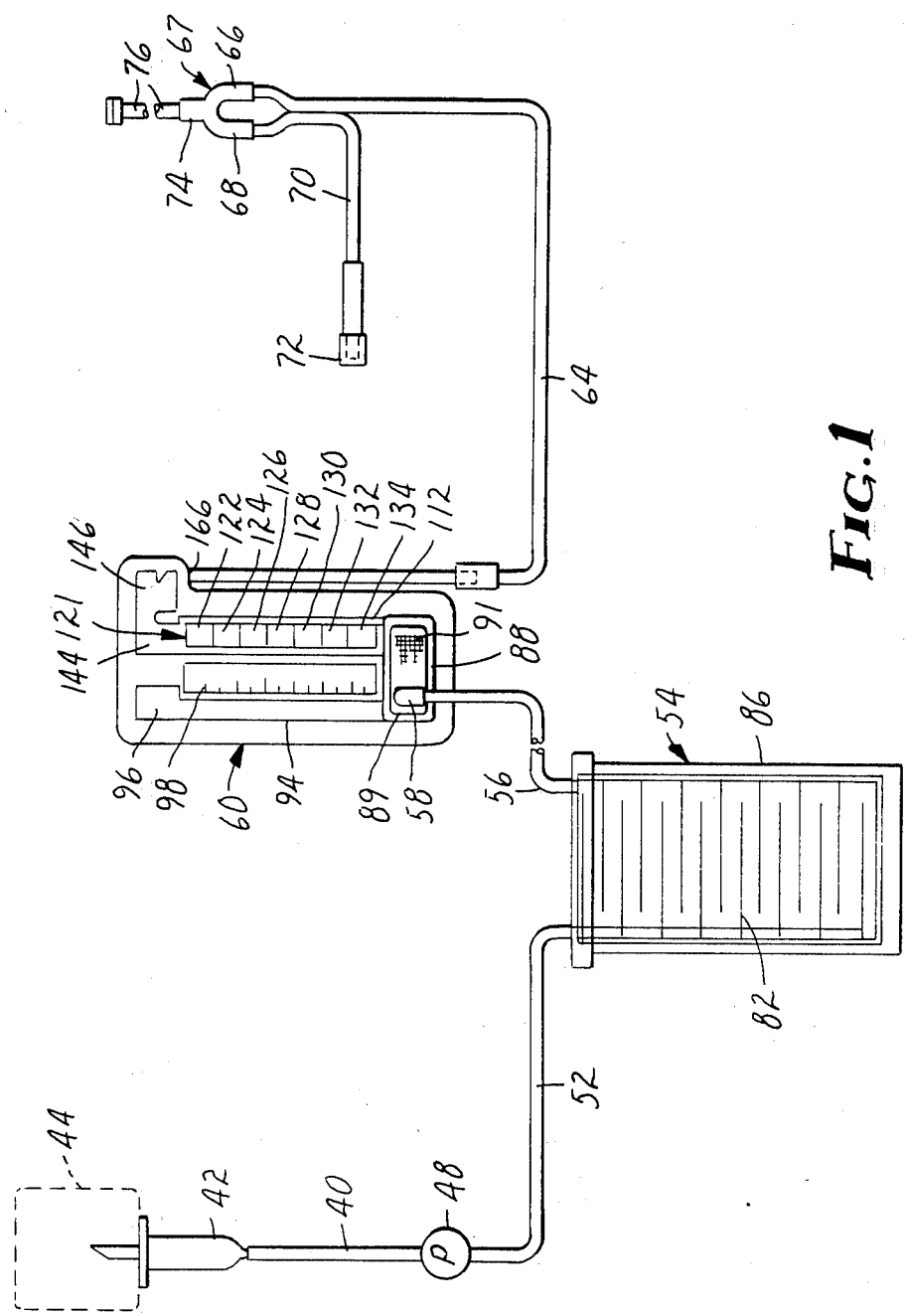
FIG. 1 is a generalized view of a crystalloid cardioplegia system showing the various elements of the system.

In FIG. 1 of the present disclosure, a crystalloid blood cardioplegia system is illustrated wherein tube 40 is connected to a drip chamber 42, above which is a drug bag or bottle 44. Tube 40 connects the drug bag 44 to a peristaltic roller pump 48. This pump is of the type generally described in a U.S. patent to DeVries, U.S. Pat. No. 3,700,301, dated Oct. 24, 1972. Flow beyond pump 48 is into tube 52 which constitutes an inlet end of a laminate cooling system 54 which has an outlet end 56 leading to the inlet 58 of monitoring module 60. This monitoring module 60 and the cooling system 54 will be described in detail below.

The monitoring module 60 has an outlet 166 connected to a tube 64 leading to one leg 66 of a Y connector 67 which has a second leg 68 connected by a tube 70. Tube 70 is connected back into drug bag 44. A cap 72 closes tube 70 prior to the connection in the system. The stem 74 of Y connector 67 connects to a tube 76 leading to a cannula (not shown) which is inserted at a suitable location to perfuse the heart when an operation is in progress.

The Cooling System

Reference has been made generally in the description directed to FIG. 1, to the laminate heat exchange cooling system 54. The cooling system 54 comprises a multiple-loop laminate 82 which is preferably made from two sheets of clear plastic film, preferably polyvinylchloride film, about 0.4 mm thick, heat sealed together to form a fluid path comprising a plurality of connected parallel horizontal rows. Laminate 82 is designed to provide maximum surface area for cooling. The multiple-loop laminate 82 can be handled as a unit and readily connected in the system. While FIG. 1 illustrates a cooling system utilizing a single multiple-loop laminate 82, it is to be understood that a plurality of multiple-loop laminates, each one connected to the other, could be utilized in cooling system 54.

Figure 7:
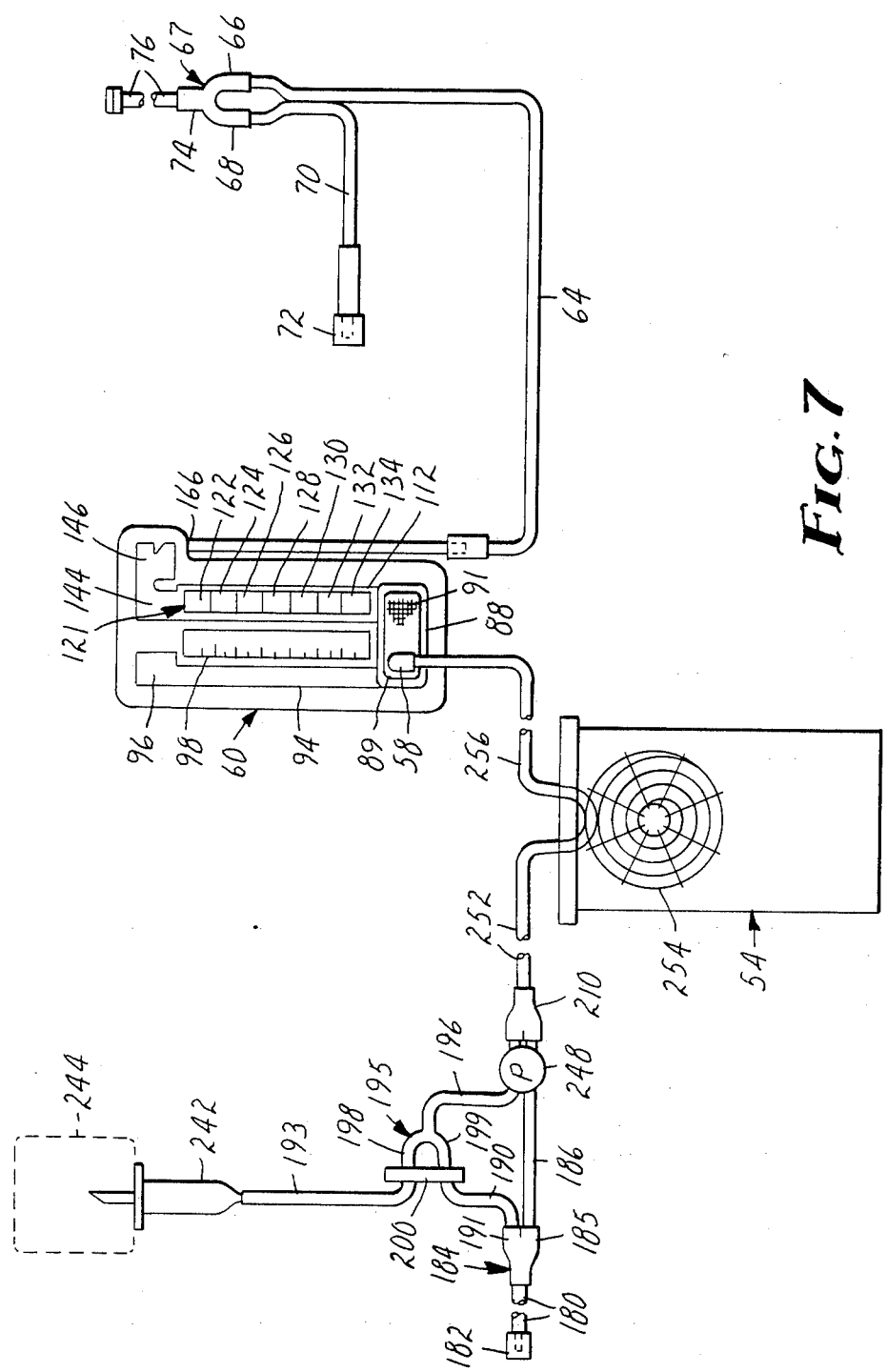
FIG. 7 is a generalized view of a blood base cardioplegia system utilizing a cooling coil assembly.

While the multiple-loop laminate 82 is considered to be the best mode, the cooling system could also comprise a continuous length of tubing which is simply wound in vertical or horizontal loops, or both. Alternatively the cooling system could comprise a coil of a continuous length of tubing wound from outside to inside, or vice versa. Such a coil is illustrated in FIG. 7, as element 254.

The multiple-loop laminate 82 is used to pass the solution of blood and/or drugs through a cooling medium. This cooling medium is preferably a "contained" cooling means, for example, a plurality of cold packs, such as those which are commercially available as "3M Coldhot Packs" from 3M Company, St. Paul, Minn., which have been cooled to between about $-25°$ C. and $-10°$ C. prior to use. Cold packs are re-useable polymeric pouches which are packed with a water-based nontoxic gel, characterized by the inclusion of a material, such as ethylene glycol, which is capable of depressing the freezing point of the gel. Alternatively the cooling medium may be ice water, or the like, or a combination of cold packs in ice water. The cooling medium is placed in tank 86, which preferably is an insulated bucket made, for example, out of styrofoam.

The multiple-loop laminate 82 provides a system wherein any contact of the cooling medium with the cardioplegic solution is prevented. The laminate 82, and the associated tubes and connectors, are preferably disposable, for one use only.

The Monitoring Module

Monitoring module 60 is a molded one-piece compact unit made from a substantially clear organic polymeric material, preferably an acrylic material such as butadiene styrene. The monitoring module is molded so that when complete it houses several components connected in series. The components of monitoring module 60 are preferably a filtering assembly, a pressure monitor, a temperature monitor and a bubble trap system. Each of these components is described in detail below. The monitoring module and the associated tubes and connectors are preferably a disposable unit for one use only.

The Filter

Referring to FIGS. 2, 3 and 4, the filtering assembly of monitoring module 60 comprises a substantially transparent plastic housing 88 bounded by a front wall 89, and a back wall 90. Front wall 89 has integrally formed therein monitoring module inlet 58. Separating front wall 89 from back wall 90 is screen 91 whose pore size is determined by the type of cardioplegia being administered. When crystalloid cardioplegia is being administered, the pore size is preferably about 5 μm in diameter, whereas for blood cardioplegia the pore size is preferably about 20 μm in diameter. In a preferred embodiment, the screen is fabricated from nylon. The screen 91 serves to remove particulate matter from the infusion fluid, thus preventing the infusion of foreign bodies into the aorta and coronary arteries. Outlets 92 and 93 for infusion fluid which has passed through the screen 91 are provided adjacent back wall 90.

The Pressure Monitor

Referring to FIGS. 1, 2 and 3, outlet 92 leads to the pressure monitoring component of monitoring module 60, which comprises an elongated manometer column 94 adapted for vertical disposition and of variable cross section, an air impervious closed reservoir chamber 96 located at the top of the column 94 and a graduated linear scale 98 disposed adjacent column 94. The constructed dimensions of column 94 and reservoir 96 are designed to permit a pressure readout, indicated by the level of infusion solution in column 94 against adjacent graduated linear scale 98. The pressure monitoring system is arranged "in-line" to be influenced by the internal pressure of the infusion fluid, and is constructed to permit substantially linear movement of infusion fluid within column 94, with substantially linear increases in pressure.

FIGS. 2 and 3 illustrate that manometer column 94 is bounded by two substantially transparent parallel side walls 100 and 101, by substantially transparent front wall 103 and by substantially transparent back wall 104. FIG. 3 illustrates that column 94 is of a variable cross section with the base of the column 105 having a greater cross sectional area than the top of the column 106 and with the cross-sectional area of the column decreasing continuously and gradually as one moves vertically up the column from base 105 to top 106. This results in back wall 104 being a shorter horizontal distance from front wall 103 at top 106 of column 94, than at base 105. Back wall 104 curves in a direction towards front wall 103 as one goes up column 94 from base 105 to top 106. Preferably back wall 104 has a slope along its length within the range of about 7 to 40.

The actual dimensions of manometer colulumn 94, which are required in order to provide a manometer column which reflects a substantially linear change in infusion system pressure by a linear change in infusion fluid level in column 94, is determined essentially by using the Ideal Gas Law $$PV = nRT$$

wherein:
P = the air pressure in the manometer column 94 and reservoir 96;
V = the total volume of air present in the manometer column 94 and the reservoir 96;
n = the number of kilogram moles of air in V;
R = the gas constant for air (8314 J/Kg mol °K.);
T = the temperature (°K.) of the air in column 94 and reservoir 96.

It should be appreciated that the Ideal Gas Law will most accurately apply to the system of the present invention, where the manometer fluid is an aqueous liquid. Where liquids which are heavier than aqueous solutions are used in manometer column 94, or where the height of column 94 is large enough so that the weight of the fluid in column 94 is more than negligible, corrections to the Ideal Gas Law must be made, as is known in the art, so that $P = nRT/V +$ the pressure exerted by the liquid in column 94.

In the system of the present invention n, R and T are held constant so that pressure P is inversely proportional to volume V. If it is desired that the pressure read out be a given value at a particular point on manometer column 94, then the volume of air required to be present in column 94 above that particular point, and in reservoir 96, can be calculated. It is desired in the present invention that the pressure readout be substantially linear along the heighth of column 94.

In the present invention, the relationship given above is exploited. The volume of the reservoir 96 is held constant, and it is presumed that the infusion fluid will not be present in reservoir 96 at any time during the operation of the cardioplegia delivery system. Additionally the length of manometer column 94, i.e. the vertical distance between the base 105 and the top 106, is constant, and the width of manometer column 94, i.e. the distance between side walls 100 and 101, is also constant. However, the cross section of the column, i.e., the horizontal distance between front wall 103 and back wall 104, varies with the change in the level of infusion fluid in column 94. Applicants have discovered that by varying the cross section of column 94 so that the cross sectional area decreases as one goes up the column and by providing reservoir 96 at the top of column 94 for receiving air dispelled from the column by rising liquid in the column, a manometer which gives a substantially linear readout of the pressure can be provided. By substantially linear, it is meant that for every 100 mm of Hg rise in the internal pressure of the system, the infusion fluid will rise in manometer column 94 a constant distance, plus or minus (±) up to about 20 percent of this constant distance. Most preferably the infusion fluid will rise a constant distance in manometer column 94, plus or minus (±) about 5 percent of this constant distance. Applicants have also discovered that if column 94 is constructed so that the cross section does not vary, the adjacent scale against which the value of the pressure is read will not be linear but will become increasingly compressed as the pressure of the system increases, thus making visual resolution more difficult.

In the present invention the dimensions, and thus the accomodated volume of air within column 94 and reservoir 96, are determined along the vertical length of column 94 according to the relationship between pressure and volume as defined by the Ideal Gas Law via a computer generated profile. For example, the computer program consists of:

(1) The total volume V of the manometer column 94 and the reservoir 96;
(2) The range of values for pressure P, which will be reflected along the length of manometer column 94, and corresponding graduated linear pressure scale 98;

(3) The increments of the manometer column 94 to be analyzed;
(4) The volume of reservoir 96;
(5) The width of manometer column 94; and
(6) The length of manometer column 94.

The computer then determines the cross section of column 94, i.e., the horizontal distance between front wall 103 and back wall 104, along the height of column 94, which will reflect a substantially linear change in the vertical height of the infusion fluid in column 94 for substantially linear changes in the infusion system pressure.

The dimensions of the pressure monitoring column 94 and reservoir 96 may vary but, as one example: The total volume of the column 94 and reservoir 96 is 31.14 cubic cm; the range of values for the pressure P is between about 760 mm of mercury (1 atm) and 1360 mm of mercury (1.8 atm) corresponding to readings on the linear pressure scale of 0 to 600 mm of mercury above atmospheric pressure; the length of column 94 is 15.24 cm; the increments of column 94 to be analyzed are 25 points along the length of the column, each point being 0.63 cm apart, thus, each point to be analyzed representing a 25 mm of Hg change in pressure P, measured along corresponding linear scale 98; the volume of reservoir 96 is 17.44 cubic cm; and the width of column 94 is 1.27 cm. A computer determination of the cross section of the manometer column at each increment in order to provide a substantially linear scale, is reported in Table I hereinbelow.

TABLE I

| Scale Pressure P (in mm Hg) | Cross Section of Column 94 (in cm) |
| --- | --- |
| 25 | 1.2322 |
| 50 | 1.1562 |
| 75 | 1.0869 |
| 100 | 1.0236 |
| 125 | 0.9657 |
| 150 | 0.9129 |
| 175 | 0.8638 |
| 200 | 0.8189 |
| 225 | 0.7775 |
| 250 | 0.7389 |
| 275 | 0.7031 |
| 300 | 0.6700 |
| 325 | 0.6391 |
| 350 | 0.6104 |
| 375 | 0.5834 |
| 400 | 0.5583 |
| 425 | 0.5347 |
| 450 | 0.5126 |
| 475 | 0.4920 |
| 500 | 0.4724 |
| 525 | 0.4539 |
| 550 | 0.4366 |
| 575 | 0.4204 |
| 600 | 0.4049 |

While reservoir 96 is shown in FIGS. 2 and 3 as square shaped and located at the top of column 94, it is appreciated that the reservoir can have any shape which will accomodate the required volume. Additionally reservoir 96 does not have to be located at the top of column 94 as long as there is some connecting air passageway (forming part of the reservoir) between the reservoir and the top of column 94.

The Temperature Monitor

Reference has been made to the temperature monitoring component of module 60, shown in FIGS. 1, 2 and 4. This temperature monitoring component comprises a column 112 which is bounded by front wall 118, back wall 120, and side walls 114 and 116. Temperature monitoring column 112 is part of the infusion fluid path and connects outlet 93 of the filter assembly with the entrance 142 to the bubble trap.

Adhered to the outer front surface 118 of the temperature monitoring column 112 so as to be in thermal contact with infusion fluid passing through column 112, is a temperature sensing strip 121 of the type which is commercially available from the American Thermometer Company, Dayton, Ohio. Temperature strip 121 comprises segments 122, 124, 126, 128, 130, 132 and 134, each segment containing a different microencapsulated liquid crystal material. The temperature sensing strip 121 is utilized to provide a visual indication of the infusion fluid temperature. The liquid crystal materials are cholesteric esters, each of which exhibits colors over a specific short temperature range. In a preferred embodiment, each segment 122 through 134 of temperature strip 121 responds to changes in temperature, sequentially reflecting a visible spectrum from blue to turquoise to straw colored, as the segment is cooled from 12° C. to below 0° C. It is preferred, since the colors reflected by the liquid crystals represent only a fraction of the incident light, the remaining portion of the incident light being scattered by the liquid crystals, that the liquid crystal microcapsules be applied to transparent film and subsequently back coated with an absorptive black material to absorb the scattered radiation. Images can be produced which appear, when the films are thermally activated, by printing windows between the film substrate and the microcapsule layer.

The printing window in segment 122 is shaped as a "12," to indicate 12° C. The window in segment 124 is shaped as a "10" to indicate 10° C. Segments 126, 128, 130, 132 and 134 are shaped as "8," "6," "4," "2," and "0," respectively, to indicate these temperatures. Upon cooling of the infusion fluid, the segments 122 through 134 exhibit the characteristic color of the liquid crystal material in that segment, through the window in that segment.

As an example, as the temperature strip 121 comes in contact with infusion fluid which is being cooled from about 12° C. to about 0° C., segment 122 will light up as a royal blue number 12. As the temperature of the infusion fluid continues to decrease, the 12 will change to turquoise. When the 12 is bright turquoise, the temperature of the fluid is 12° C. As the fluid's temperature drops below 12° C., the 10 in segment 124 becomes royal blue, then turquoise, and the 12 in segment 122 becomes a straw color. This pattern continues through segments 126, 128, 130, 132 and 134 as the infusion fluid is cooled to 0° C.

The dimensions of temperature monitoring column 112 may vary but, as one example, the column has a height of about 140 mm, a width of about 28 mm, and a depth, i.e., the distance between front wall 118 and back wall 120, of about 4 mm.

The Bubble Trap

Reference has been made to the bubble trap of monitoring module 60. Referring to FIGS. 2, 4, 5 and 6, the bubble trap is preferably constructed of substantially transparent plastic and includes primary chamber 144, and secondary chamber 146, with the two chambers separated by integral dam 148. Primary chamber 144 includes an infusion fluid entrance way 142 which, preferably, is at the top of temperature monitoring column 112, and at the bottom of primary chamber 144. Primary chamber 144 is bounded by upright front wall 118, angled back wall 150, upright back wall 152, upright side wall 153, dam 148, and top wall 154. Upright side wall 153 is disposed opposite upright dam 148. Back wall 152 is shown to be substantially parallel to front wall 118. Angled back wall 150 lies at about a 47° angle to back wall 120 of temperature monitoring column 112. Primary chamber 144 is shaped so that when infusion fluid enters the chamber from entrance 142, its velocity decelerates due to the sharp back angle of back wall 150. The velocity of the infusion fluid is measured in cm/min along the flow path of the infusion fluid. This relative deceleration and "pooling" of the infusion fluid allows bubbles to buoy to the surface of the fluid before passing over dam 148 and into secondary chamber 146. Accordingly, the primary chamber 144 can have any shape that will provide it with a greater cross-sectional area than entrance way 142, so that infusion fluid entering the primary chamber from the entrance way will decelerate.

Secondary chamber 146 is bounded by upright front wall 158, upright back wall 160, upright exterior side wall 162, bottom wall 164, top wall 154, and dam 148. Top wall 154 includes a vent means 156 for purging accumulated air in the system. An outlet 166 for infusion fluid leading to the heart cannula is provided in bottom wall 164. The area of the bubble trap above the top 168 of dam 148 provides a passageway for infusion fluid between primary chamber 144 and secondary chamber 146.

Upright exterior side wall 162 has integrally formed therein shelf 170. Shelf 170 includes ledge 172, supported by support wall 174. Ledge 172 extends into secondary chamber 146, and is disposed in a direction which is substantially perpendicular to both exterior side wall 162 and dam 148. The width of ledge 172, i.e., the horizontal distance that the ledge extends into secondary chamber 146 measured from exterior side wall 162, is about 45 percent of the entire width of secondary chamber 146, i.e., the horizontal distance measured between exterior surface 176 of dam 148 and exterior side wall 162. Applicants have discovered that the width of ledge 172 should preferably be no less than about 15 percent of the width of secondary chamber 146, in order to provide an effective bubble trap. However, Applicants have also discovered that the width of the ledge should preferably be no greater than 85 percent of the width of the secondary chamber in order to prevent failure of the bubble trap in low priming or high flow situations.

Shelf 170 preferably spans the entire distance between front wall 158 and back wall 160. However, the shelf length may be reduced to expand only about 50 percent of this distance if the flow rates of the infusion fluid are appropriately reduced.

The location of shelf 170 on exterior side wall 162 can vary, however, ledge 172 is preferably located on exterior side wall 162 so that it is not higher than the top 168 of dam 148. Additionally, shelf 170 must be located on exterior wall 162 no lower than that which is necessary to clear outlet 166. As one example, ledge 172 is about 5 mm below top 168 of dam 148.

Support wall 174 extends between ledge 172 and exterior side wall 162. Preferably support wall 174 is shaped so that it lies at an acute angle to ledge 172. Most preferably support wall 174 lies at an angle of about 30° to ledge 172, however, it is appreciated that this angle will vary with the design of shelf 170. An angled support wall has been found to aid in priming the bubble trap by reducing the chance that air may be trapped beneath ledge 172. It is noted that while shelf 170 has an angular shape, any shaped piece which is capable of diverting flow can be utilized as shelf 170. For example, shelf 170 could have a square shape or arched shape, etc.

The dimensions of bubble trap 140 may vary but, as one example, a bubble trap of the invention has the following dimensions:

Horizontal distance between front wall 118 and back wall 152 = about 25.4 mm.
Horizontal distance between exterior side wall 153 and dam 148 = about 19.1 mm.
Vertical distance between top wall 154 and fluid entrance 142 = about 45.5 mm.
Angle which back wall 150 makes with back wall 120 of temperature monitoring column 112 = about 47°.
Horizontal distance between front wall 158 and back wall 160 = about 25.4 mm.
Horizontal distance between exterior side wall 162 and dam 148 = about 27.9 mm.
Vertical distance between top wall 154 and bottom wall 164 = about 38.1 mm.
Width of ledge 172 = about 12.7 mm.
Angle at which support wall 174 meets ledge 172 = about 30°.
Vertical distance between top of dam 168 and top wall 154 = about 15.3 mm.
Horizontal distance between exterior side wall 153 and exterior side wall 162 = about 55.9 mm.
Diameter of outlet 166 in bottom wall 164 = about 3.4 mm.
Diameter of vent 156 in top wall 154 = about 3.9 mm.

The Operation of the Apparatus

The system shown in FIG. 1 is called a crystalloid cardioplegia system. Cold packs or ice and water are first placed in the tank 86. Tube 40 is connected to drug bag 44 and the roller pump 48 is started. Suitable liquid medication will pass through the laminate 82 and be cooled to preferably between about 10° C. and 2° C., most preferably to about 4° C. After passing through laminate 82 the infusion fluid enters monitoring module 60 through inlet 58. The infusion fluid first passes through screen 91 in filter housing 88, and particulate matter is removed. A minor portion of the infusion fluid flows through outlet 92 and into manometer column 94. The height that the infusion fluid reaches in manometer column 94 is a function of the pressure of the infusion fluid passing through the system. The pressure of the system can then be read off corresponding linear pressure scale 98.

After equilibration of the manometer column 94, the infusion fluid flows through outlet 93 to in-line temperature monitoring column 112. The temperature of the infusion fluid in column 112 may be read off liquid crystal temperature strip 121. Because the temperature monitoring column 112 is relatively narrow, the fluid traveling through it is moving at a relatively high velocity, as compared to the velocity of the fluid as it passes through chambers 144 and 146 of the bubble trap. The average velocity of the fluid in column 112 varies with the flow rate but is preferably from about 5 cm/min to 1,000 cm/min, and is most preferably from about 50 cm/min to 700 cm/min.

After passing through temperature monitoring column 112, the infusion fluid enters the bubble trap through entrance 142. The infusion fluid first enters primary chamber 144. Due to the increased cross sectional area of chamber 144, as compared with column 112, fluid entering chamber 144 immediately decelerates. Preferably, the average velocity of the infusion fluid decreases by at least about 200 percent when it passes from entrance way 142 into primary chamber 144, and most preferably the average velocity decreases by about 500 percent. This relative deceleration and pooling of the fluid allows air bubbles contained in the infusion fluid to buoy to the surface of the liquid before passing through secondary chamber 146 to outlet 166.

Dam 148 is provided between chambers 144 and 146 to provide the longest possible flow path for the infusion fluid in the bubble trap, and to give bubbles an increased opportunity to reach the surface of the infusion fluid before the fluid enters outlet 166. Shelf 170 is provided in secondary chamber 146 because as the flow rate of the infusion fluid increases above about 150 ml/min the fluid velocity and bubble momentum tend to overcome the effects of buoyancy. Shelf 170 prevents any shunting of air bubbles to outlet 166 by re-directing flow to the surface. Shelf 170 also functions to reduce the priming volume of the system, eliminate dead spaces, and shield outlet 166.

Outlet 166 in bottom wall 164 of secondary chamber 146 is located beneath shelf 170 and in the farthest corner of the trap relative to entrance way 142, so as to provide the longest possible flow path for the infusion fluid in the bubble trap, and to give bubbles an increased opportunity to reach the surface of the infusion fluid before the fluid enters the outlet leading to the patient.

Preferably the bubble trap is primed so that the infusion fluid entirely fills chambers 144 and 146. This allows the maximum displacement of fluid and the maximum time period before bubble trap failure. As bubbles rise to the surface of the liquid in chambers 144 and 146, this will reflect in the level of the liquid in the trap. If the infusion fluid level falls in the bubble trap, this may be an indication of a breakdown in the system either because of a dry medication bag or a leak upstream of the pump. If the level of fluid in the bubble trap drops to the top 168 of dam 148, the system may be shut down momentarily to locate the source of the problem, and then restarted.

It is preferred that the flow rate of the infusion fluid be between about 5 ml/min and 1 liter/min, and most preferably between about 5 ml/min and 500 ml/min, in order for the bubble trap to be most effective in removing air from the infusion fluid.

Debubbled infusion fluid will outflow at outlet 166, travel through tube 64 and reach the Y connector 67. From leg 66 of Y connector 67 the infusion fluid will travel through stem 74 and tube 76 to a suitable cannula into the heart. Alternatively, if desired, suitable closure clamps (not shown) can divert the infusion fluid through leg 68 of Y connector 67, through bypass tube 70 and back to drug bag 44.

In FIG. 7, a proportional blood cardioplegia system is illustrated wherein the tube 180, shown in the drawing with a temporary cap 182, is to be connected to a source of oxygenated arterial blood and leads to a Y connector 184, one leg 185 of which connects through a tube 186 to a peristaltic roller pump 248. This pump is of the type generally described in a U.S. patent to DeVries, U.S. Pat. No. 3,700,301, dated Oct. 24, 1972, but has a suitable race and guides for a double tube application.

A second tube 190 from leg 191 of the Y connector 184 leads to a leg 199 of a Y connector which joins also with a tube 193 at leg 198. Tube 193 is connected to a drip chamber 242, above which is a drug bag or bottle 244. The tubes 190 and 193 are joined to a Y connector 195 which joins with a tube 196 leading through the roller pump 248 in parallel with the tube 186. The legs 198 and 199 of the Y connector 195 are controlled by a valve 200 which is movable to close one or the other of the legs selectively. A two-position valve of this nature is shown in commonly assigned U.S. Pat. No. 4,433,971 and U.S. Pat. No. 4,427,009 both of which are incorporated herein by reference. The valve can be an overcenter type wherein a spring serves to hold the valve in one position or the other to squeeze the tubes 193 and 190 selectively to a closed position.

The tube portion 190 serves as a blood by-pass when tube 193 is occluded, thus preventing a suction collapse of tube 196 and possible degasification due to this suction.

The valve 200 is used to close by-pass tube 190 when medication is being fed through tube 193, leg 198, and tube 196. When tube 193 is closed by valve 200, the by-pass is open.

Tubes 186 and 196 merge flow beyond pump 248 at a Y connector 210 into a tube 252 which constitutes an inlet end of a cooling coil cooling system 254 which has an outlet end 256 leading to the inlet 58 of monitoring module 60. Other elements of this system are essentially the same as previously described, except that tube 70 is connected to a cardiotomy reservoir.

What is claimed is:

1. A bubble trap for removing bubbles from a liquid comprising:
   (a) a primary chamber having an entrance way for liquid disposed at the bottom, said primary chamber capable of providing a passageway for liquid leaving said entrance way, and said primary chamber having a greater cross-sectional area than said entrance way, such that when liquid enters said primary chamber from said entrance way the average velocity of the liquid is caused to decelerate; and
   (b) a secondary chamber separated from said primary chamber by a dam, the area above said dam providing a passageway for liquid flowing from said primary chamber to said secondary chamber, said secondary chamber bounded by said dam, an exterior side wall which is disposed opposite said dam, a front wall and back wall which is disposed opposite said front wall, and said secondary chamber having a shelf extending from said exterior wall into said secondary chamber in a direction towards said dam but not extending so far into said secondary chamber as to block the passage of liquids through said secondary chamber, and said secondary chamber having an outlet for liquid disposed at the bottom of said secondary chamber said shelf capable of re-directing liquid flow in said secondary chamber away from said outlet and towards the top of said secondary chamber.

2. A bubble trap for removing bubbles from cardioplegia medication or a mixture of arterial blood and medication in a cardioplegia system, said bubble trap having an infusion fluid inlet connected to the supply of cardioplegia infusion fluid and an outlet leading to the heart cannula, and said bubble trap comprising:

(a) a primary chamber having an entrance way for infusion fluid disposed at the bottom, said entrance way adapted for connection with said infusion fluid inlet, said primary chamber capable of providing a passageway for infusion fluid leaving said entrance way, and said primary chamber having a greater cross-sectional area than said entrance way, such that when infusion fluid enters said primary chamber from said entrance way the average velocity of said infusion fluid is caused to decelerate; and (b) a secondary chamber separated from said primary chamber by a dam, the area above said dam providing a passageway for infusion fluid flowing from said primary chamber to said secondary chamber, said secondary chamber bounded by said dam, an exterior side wall which is disposed opposite said dam, a front wall and a back wall which is disposed opposite said front wall, and said secondary chamber having a shelf extending from said exterior wall into said secondary chamber in a direction towards said dam but not extending so far into said secondary chamber as to block the passage of infusion fluid through said secondary chamber, and said secondary chamber having said outlet for infusion fluid disposed at the bottom of said secondary chamber said shelf capable of re-directing infusion fluid flow in said secondary chamber away from said outlet and towards the top of said secondary chamber.

3. The bubble trap of claim 2 wherein at least a portion of said bubble trap is transparent to provide a visual indication of the air removed from said infusion fluid.

4. The bubble trap of claim 2 wherein said bubble trap has a top wall with a vent means for purging accumulated air in said system.

5. The bubble trap of claim 2 wherein said shelf extends into said secondary chamber to such an extent that said shelf spans at least 50 percent of the distance between said front wall of said secondary chamber and said back wall of said secondary chamber.

6. The bubble trap of claim 5 wherein said shelf is comprised of a ledge portion which is disposed in a direction substantially perpendicular to said exterior side wall of said secondary chamber, and a support wall underlying and supporting said shelf.

7. The bubble trap of claim 6 wherein said support wall extends between said ledge and said exterior side wall of said secondary chamber, and wherein said support wall is disposed at an acute angle with respect to said ledge.

8. The bubble trap of claim 6 wherein said ledge is disposed in said secondary chamber so that it is located between the top of said dam and the bottom of said secondary chamber.

9. The bubble trap of claim 2 wherein the dimensions of said primary chamber are such that the average velocity of said infusion fluid decelerates by at least about 200 percent when the fluid enters said primary chamber from said entrance way.

10. The bubble trap of claim 2 wherein said outlet for infusion fluid in the bottom of said secondary chamber is located beneath said shelf and on the side of said secondary chamber furthest from said entrance way.

11. The bubble trap of claim 2 wherein said shelf extends to such an extent that the distance between said shelf and said dam is between about 85 and 15 percent of the distance between said dam and said exterior side wall.

12. An improved cardioplegia system in which cardioplegia medication or a mixture of arterial blood and medication is delivered to the heart of a patient during open heart surgery, wherein the improvement comprises a one-piece monitoring module, said monitoring module having an inlet connected to the supply of cardioplegic infusion fluid and an outlet leading to the heart cannula, and said monitoring module comprising:

(a) a pressure measuring device for measuring the internal pressure of said infusion fluid in said cardioplegia system;

(b) a temperature measuring device for measuring the temperature of said infusion fluid; and (c) a bubble trap for removing bubbles from said infusion fluid before it passes through said outlet to said heart cannula, said bubble trap comprising:

(1) a primary chamber having an entrance way for infusion fluid disposed at the bottom, said primary chamber capable of providing a passageway for infusion fluid leaving said entrance way, and said primary chamber having a greater cross-sectional area than said entrance way, such that when infusion fluid enters said primary chamber from entrance way the average velocity of said infusion fluid is caused to decelerate; and (2) a secondary chamber separated from said primary chamber by a dam, the area above said dam providing a passageway for infusion fluid flowing from said primary chamber to said secondary chamber bounded by said dam, an exterior side wall which is disposed opposite said dam, a front wall and a back wall which is disposed opposite said front wall, and said secondary chamber having a shelf extending from said exterior wall into said secondary chamber in a direction towards said dam but not extending so far into said secondary chamber as to block the passage of infusion fluid through said secondary chamber, and said secondary chamber having said outlet for infusion fluid disposed at the bottom of said secondary chamber said shelf capable of re-directing infusion fluid flow in said secondary chamber away from said outlet and towards the top of said secondary chamber.

13. The improved cardioplegia system of claim 12 wherein said pressure measuring device comprises a single-leg manometer column connected with said supply of cardioplegic infusion fluid, said column being substantially transparent along at least a portion of its length to provide for viewing the level of infusion fluid in said column, and a graduated linear scale disposed adjacent said column for reading the level of infusion fluid contained within said column as a representation of internal infusion fluid pressure at any given time.

14. The improved cardioplegia system of claim 12 wherein said temperature monitoring device comprises a temperature monitoring column through which the infusion fluid passes, and a liquid crystal temperature sensing strip disposed adjacent said column and being in thermal contact with the infusion fluid passing through said column, said liquid crystal temperature sensing strip capable of providing a visual indication of the infusion fluid temperature.

15. The improved cardioplegia system of claim 12 wherein said one-piece monitoring module additionally comprises a filtering assembly capable of removing particulate matter from said infusion fluid.

16. The improved cardioplegia system of claim 12 wherein said monitoring module is constructed from a clear organic polymeric material, and said bubble trap is capable of providing a visual indication of the increase of air in said cardioplegia system.

17. The improved cardioplegia system of claim 12 wherein said system additionally comprises a cooling system which comprises:
   (a) a cooling medium;
   (b) a cooling tank to hold said cooling medium; and
   (c) at least one multiple-loop laminate supported in said tank, said laminate constructed from a flexible organic polymeric film so as to form a path for said infusion fluid comprising a plurality of connected substantially parallel rows, and having inlet and outlet ends for said infusion fluid.

18. The improved cardioplegia system of claim 17 wherein said cooling medium comprises at least one pouch packed with a water-based nontoxic gel having a depressed freezing point.

19. A method of debubbling a liquid comprising the steps of:
   (a) passing the liquid through an entrance way into a primary chamber, said entrance way being connected at the bottom of said primary chamber, and said primary chamber having a greater cross-sectional area than said entrance way, so that the average velocity of liquid entering said primary chamber from said entrance way decelerates;
   (b) causing said liquid to discharge into a secondary chamber separated from said primary chamber by a dam, the area above said dam providing the passageway for said liquid from said primary chamber to said secondary chamber, said secondary chamber bounded by said dam, an exterior side wall which is disposed opposite said dam, a front wall and a back wall which is disposed opposite said front wall, and said secondary chamber having a shelf extending from said exterior wall into said secondary chamber in a direction towards said dam but not extending so far into said secondary chamber as to block the passage of liquids through said secondary chamber, and said secondary chamber having an outlet for liquid disposed at the bottom of said secondary chamber said shelf capable of re-directing liquid flow in said secondary chamber away from said outlet and towards the top of said secondary chamber; and
   (c) discharging said liquid through said outlet at the bottom of said secondary chamber.

* * * * *